(12) United States Patent
DeCarlo

(10) Patent No.: US 8,469,953 B2  
(45) Date of Patent: Jun. 25, 2013

(54) TWIN SEALING CHAMBER HUB

(75) Inventor: Arnold V. DeCarlo, Frederick, CO (US)

(73) Assignee: Covidien LP, Mansfield, MA (US)

( * ) Notice: Subject to any disclaimer, the term of this patent is extended or adjusted under 35 U.S.C. 154(b) by 629 days.

(21) Appl. No.: 12/619,323

(22) Filed: Nov. 16, 2009

(65) Prior Publication Data

US 2011/0118730 A1 May 19, 2011

(51) Int. Cl.
*A61B 18/18* (2006.01)

(52) U.S. Cl.
USPC ............................ 606/41; 607/101

(58) Field of Classification Search
USPC ............................ 606/41; 607/101
See application file for complete search history.

(56) References Cited

U.S. PATENT DOCUMENTS

| | | | |
|---|---|---|---|
| 5,129,396 A | 7/1992 | Rosen | |
| 5,167,619 A | 12/1992 | Wuchinich | |
| 5,312,400 A * | 5/1994 | Bales et al. | 606/41 |
| 5,507,744 A * | 4/1996 | Tay et al. | 606/50 |
| 6,494,892 B1 * | 12/2002 | Ireland et al. | 606/180 |
| 7,766,844 B2 * | 8/2010 | Sjostrom | 600/571 |
| 7,981,051 B2 * | 7/2011 | Quick et al. | 600/566 |
| 2003/0004508 A1 * | 1/2003 | Morgan et al. | 606/41 |
| 2005/0245920 A1 * | 11/2005 | Vitullo et al. | 606/33 |
| 2006/0085054 A1 | 4/2006 | Zikorus et al. | |
| 2007/0073285 A1 | 3/2007 | Peterson | |
| 2007/0208351 A1 * | 9/2007 | Turner et al. | 606/108 |
| 2008/0027424 A1 * | 1/2008 | DeCarlo et al. | 606/41 |
| 2008/0161890 A1 * | 7/2008 | Lafontaine | 607/105 |
| 2008/0287946 A1 * | 11/2008 | DeCarlo et al. | 606/41 |
| 2009/0138010 A1 * | 5/2009 | DeCarlo | 606/41 |
| 2009/0187180 A1 | 7/2009 | Brannan | |
| 2009/0222002 A1 | 9/2009 | Bonn et al. | |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |

(Continued)

OTHER PUBLICATIONS

U.S. Appl. No. 12/129,482, filed May 29, 2008.

(Continued)

*Primary Examiner* — Linda Dvorak
*Assistant Examiner* — Jocelyn D Ram

(57) ABSTRACT

Devices and methods for cooling microwave antennae and microwave hub construction are disclosed herein. The cooling system and hub can be utilized with a variety of microwave antenna types. A microwave hub is utilized to provide cooling fluids to a microwave antenna. The hub is constructed using no glue or adhesive for holding the different parts of the chambers in place. O-rings provide an increased reliability and consistency for fluid-tight seals in the hub. The various parts of the hub are form fitted and work together with the o-rings.

7 Claims, 3 Drawing Sheets

FOREIGN PATENT DOCUMENTS

| | | |
|---|---|---|
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |

OTHER PUBLICATIONS

U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedance" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.
Herman at al., "Laparoscopic Intestinal Resection With the LigaSure™ VesselSealing System: A Case Report" Innovations That Work, Feb. 2002.
Humphries Jr. et al., "Finite•Element Codes to Model Electrical Heating and Non-LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
MEDTREX Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et aI., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.

European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 10014675 dated Feb. 24, 2011 (7 pages).

\* cited by examiner

TWIN SEALING CHAMBER HUB

BACKGROUND

The present invention relates generally to the field of ablation. More particularly, the present invention relates to apparatus, systems, and methods for cooling electrosurgical probes or microwave antennas. More particularly, the present invention relates to methods of assembly of electro-surgery and microwave antennas.

During the course of surgical procedures, it is often necessary for medical personnel to utilize electrosurgical instruments to ablate tissue in a body. High frequency probes or antennas are often utilized to ablate tissue in a body. In use, the probes or antennas are connected to a high frequency power source to heat body tissue when inserted into the tissue. Among the drawbacks of such devices is the potential that the probes or antennas will overheat, thus causing damage to the bodily tissue or causing damage to the instrument. A cooling system may be used in conjunction with the instrument to provide cooling of the instrument and often to the tissue adjacent to the instrument so as to provide optimal thermal characteristics in the instrument and the tissue. In the event that the heat is not dissipated in the instrument, charring of the tissue or failure of the instrument can occur.

Surgical systems exist that provide cooling systems for the instrument. Existing systems provide a flow of a cooling fluid to the instrument thus cooling the instrument and potentially the tissue adjacent to or abutting the targeted tissue. These systems generally employ a mechanism whereby the cooling fluid flows into a hub through a chamber. The fluid flows into a lumen path and down to the tip of the instrument, providing cooling along the shaft of the instrument. The fluid returns to another chamber in the hub and exits through a fluid egress channel.

The chambers, lumen paths, hub and seals of a hub are constructed in a manner requiring an adhesive, or glue, to maintain their integrity during stress. It is known that during use, pressure is created in the interior of the hub causing stress at the seal locations, in the chambers and at the connection points. However, adhesives or glue can be inconsistent and unreliable. Not only can adhesives breakdown under stress or heat conditions, but the application of the adhesives during the manufacturing process can be inconsistent. These breakdowns and inconsistencies can lead to malfunctions and inadequate cooling.

SUMMARY OF THE INVENTION

According to one embodiment of the present invention, there is provided an electrosurgical hub. The hub is adapted to provide cooling fluid to probes that extend from a distal end of the hub. The probes are utilized by medical personnel to ablate tissue in a body.

Two chambers and a dual path lumen provide cooling liquid to a probe. Cooling fluid enters into the hub and is channeled from a first chamber through a lumen path which transports the fluid to the probes for cooling purposes. An insert defines the boundary for the first chamber and causes the cooling fluid to spin, thus reducing the presence of air bubbles. The insert is adapted to accommodate a first o-ring to form a seal between the first chamber and a second chamber. A connector connected to the probes which conducts power to the probe, is also adapted to accommodate a second o-ring to form a seal on the back side of the first chamber.

The cooling fluid returns through a second lumen path and enters a second chamber. A plug is adapted to accommodate a third o-ring to form a second seal on the second chamber. The plug has an annular ring utilized to center the plug in the hub and maintain the third o-ring in position during high stress conditions.

In general, the apparatus of the present invention is directed to a twin sealing chamber ablation hub constructed without glues or adhesives. The system offers a method of construction that improves reliability in the chamber seals. The apparatus includes a geometry whereby air bubbles which can cause hot spots on the ablation probe are substantially removed from the cooling liquid.

There is accordingly a need for an electrosurgical hub that provides consistency in manufactured result as well as reliability under stress conditions. There is a need for a hub that overcomes the breakdown of adhesives. There is also a need for a hub that allows for consistent manufacturing procedures.

DETAILED DESCRIPTION OF THE EMBODIMENTS

In one embodiment of the invention, a twin chamber microwave ablation hub comprises a plurality of inserts and o-rings causing seals between the chambers. A first chamber provides fluidic connection to an input port and a second chamber provides fluidic connection to an exit port. A dual path lumen provides fluidic connection from the first chamber to the second chamber. The first and second chambers are adapted to minimize the presence of air bubbles in a cooling fluid as the fluid travels through the input port and the first chamber, through a first path in the lumen to the distal end of an ablation probe. The cooling fluid returns via a second path in the lumen to the second chamber and exits the hub via the exit port. The first path and second path are concentric.

The term "probe" is not limited to the present embodiment or depiction. Naturally, the efficacy of the present invention may be optimized by different types of devices intended to facilitate energy focalization in a body, such as electrodes, antennas or other suitable device. The term "probe" is used to include any device, mechanism or structure capable of being inserted into a body and allowing an energy source to be focalized for ablation or other medical treatment.

Figure 1:
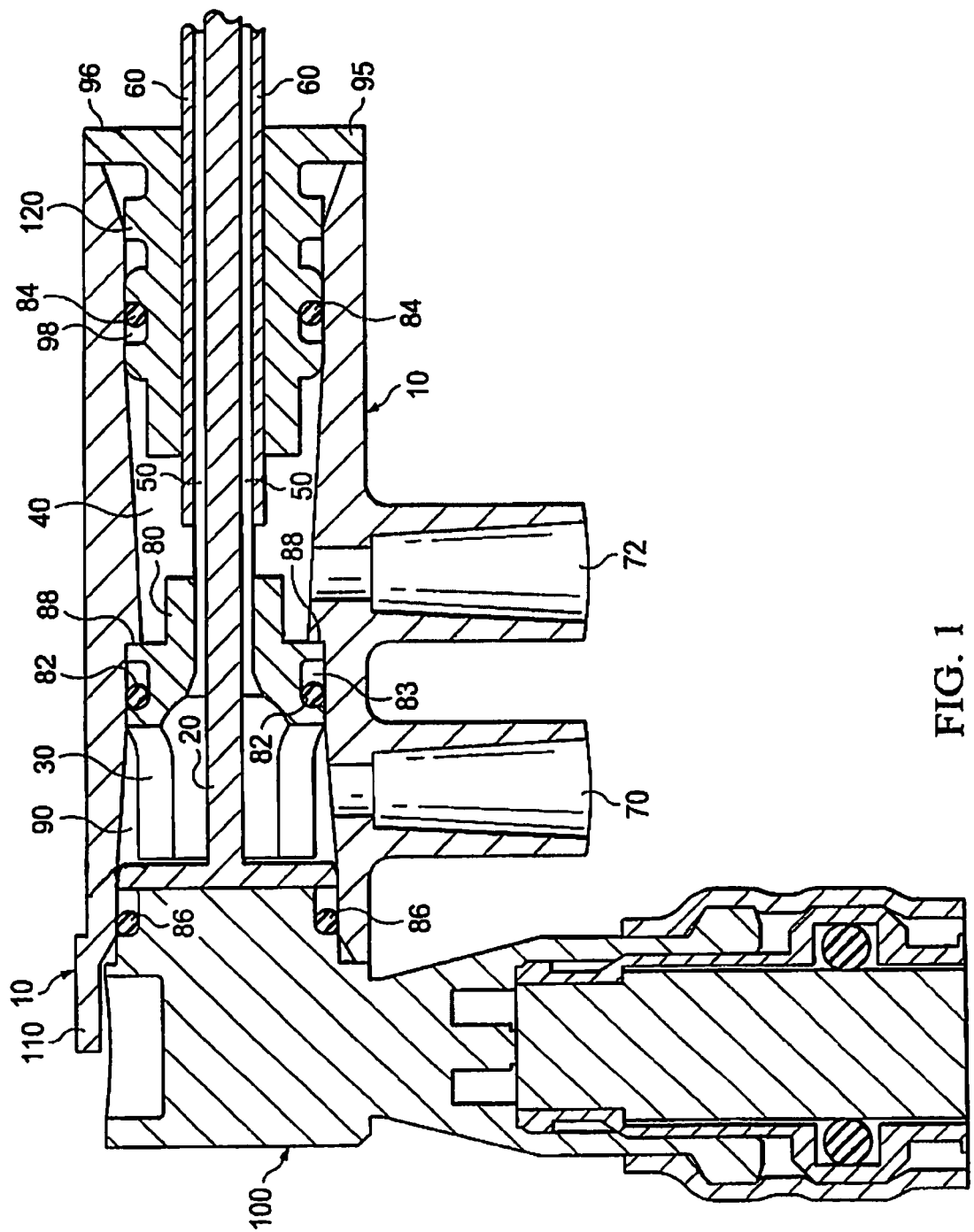
FIG. 1 is a view of an embodiment of the invention showing twin chambers in a hub with inserts providing separation of the chambers.

FIG. 1 is a view of an embodiment of the invention showing a hub 10 and probe 20. Hub 10 comprises a first chamber 30, a second chamber 40, a first lumen path 50, a second lumen path 60, a first port 70 and a second port 72. First port 70 fluidicly couples to first chamber 30. First chamber 30 fluidicly couples to first lumen path 50. First lumen path 50 extends along a substantial portion of the probe 20. The second lumen path 60 extends around and along the first lumen path 50 and fluidicly couples with the second chamber 40.

The first 30 and second 40 chambers are defined by inserts inside the hub 10. A first insert 80 fits inside one end of hub 10. In one embodiment, the first chamber 30 is at one end by the first insert toward the handle end of the hub 10. The first insert 80 is positioned against stops 88. Stops 88 provide a positioning stop on the interior walls 90 of the hub for the first insert 80. The stops 88 provide a more precise positioning for the first insert 80 and eliminate placement guesswork. This allows for ease of insertion by providing a physical indicator of the proper insertion position.

The interior walls 90 of the hub 10 may be graduated so that they are of decreasing diameter from the handle end of the hub to the stops 88. This also allows for ease of insertion as well as precision in placement. In an embodiment of the invention, the graduation of the interior walls ceases prior to the stop 88, creating a zone where the interior wall 90 is flat. As discussed below, the flat zone in wall 90 allows for more reliable sealing of the first chamber 30.

An o-ring 82 is positioned in space 83 of the insert first 80. It is understood that the space 83 is a groove or other indentation in the first insert 80. When the first insert 80 in inserted into the hub 10 to the proper depth, the o-ring 82 will contact the flat portion of the interior wall. The o-ring 82 provides for continued sealing in the event of slight movement or slight inaccuracies in the manufacture of the first insert 80 or hub 10. The flat area allows for continued contact of the o-ring 82 in the event of slight movement. The o-ring 82 provides a water-tight seal for the first chamber 30. Accordingly, any cooling fluid will not flow around chamber 30 and past stops 88.

The second chamber 40 is positioned distally of the first chamber 30, toward the probe end of the hub 10. As noted above, the first insert 80 is inserted inside the hub 10 to stops 88. One end of the second chamber 40 is formed by the back side of the first insert 80. The second chamber 40 is completed by second insert 95 opposite the first insert 80. Insert 95 is inserted into the distal end of the hub 10 opposite the first insert 80. In one embodiment, the interior walls of the hub 10 at the distal end are graduated so that they are of decreasing diameter from the end of hub 10 to the interior. The graduation of the interior walls ceases at the location where the o-ring 84 reside. This creates a flat zone which allows continued sealing in the event of slight movement or slight inaccuracies in the manufacture of the insert 95 or hub 10. The graduation of the interior walls of hub 10 allow for ease of insertion of insert 95 as well as precision in placement.

The insert 95 comprises an end portion 96 adapted to provide a stopping mechanism. The end portion 96 acts to contact the end of hub 10. End portion 96 abuts the hub 10 and provides for precision in placement. An o-ring 84 is positioned in the second insert 95 to contact the interior wall 90 when the second insert 95 is inserted into the hub 10. The O-ring 84 is positioned in space 98 of the second insert 95. The o-ring 84 provides a water-tight seal for the second chamber 40. Accordingly, cooling fluid will not flow around chamber 40 or into the first chamber 30. The second insert 95 is molded to hub 10 on the opposite end of the hub 10 from handle 100. The molding maintains closure and sealing during high pressure conditions.

When the second insert 95 is inserted, a centered position in the hub is desired to help eliminate any leakage that may occur otherwise. An annular ring 120 is utilized to maintain a centered position of the second insert 95 and the o-ring 84 within the hub 10. When the second insert 95 in inserted so that the end portion 96 abuts the hub 10, the annular ring 120 contacts the interior wall 90 and disallows movement of the second insert 95.

A third o-ring 86 is positioned in handle 100. The third o-ring 86 provides a fluid seal on the back side of chamber 30. The handle 100 in inserted into the end of the hub 10 opposing the position of insert 95. In an embodiment, the handle 100 is molded to hub 10. The handle 100 is adapted to abut or closely abut first insert 80. The position of insert 80 is maintained by the handle 100 under high pressure conditions.

Handle 100 connects to the probe 20. Box 110 disallows improper insertion of the handle 100 and ensures that the probe 20 is connected properly through the hub 10. Box 110 protrudes away from the hub to disallow upside down insertion of the handle 100. The probe 20 protrudes through the first 30 and second 40 chambers and first 80 and second 95 inserts.

Figure 2:
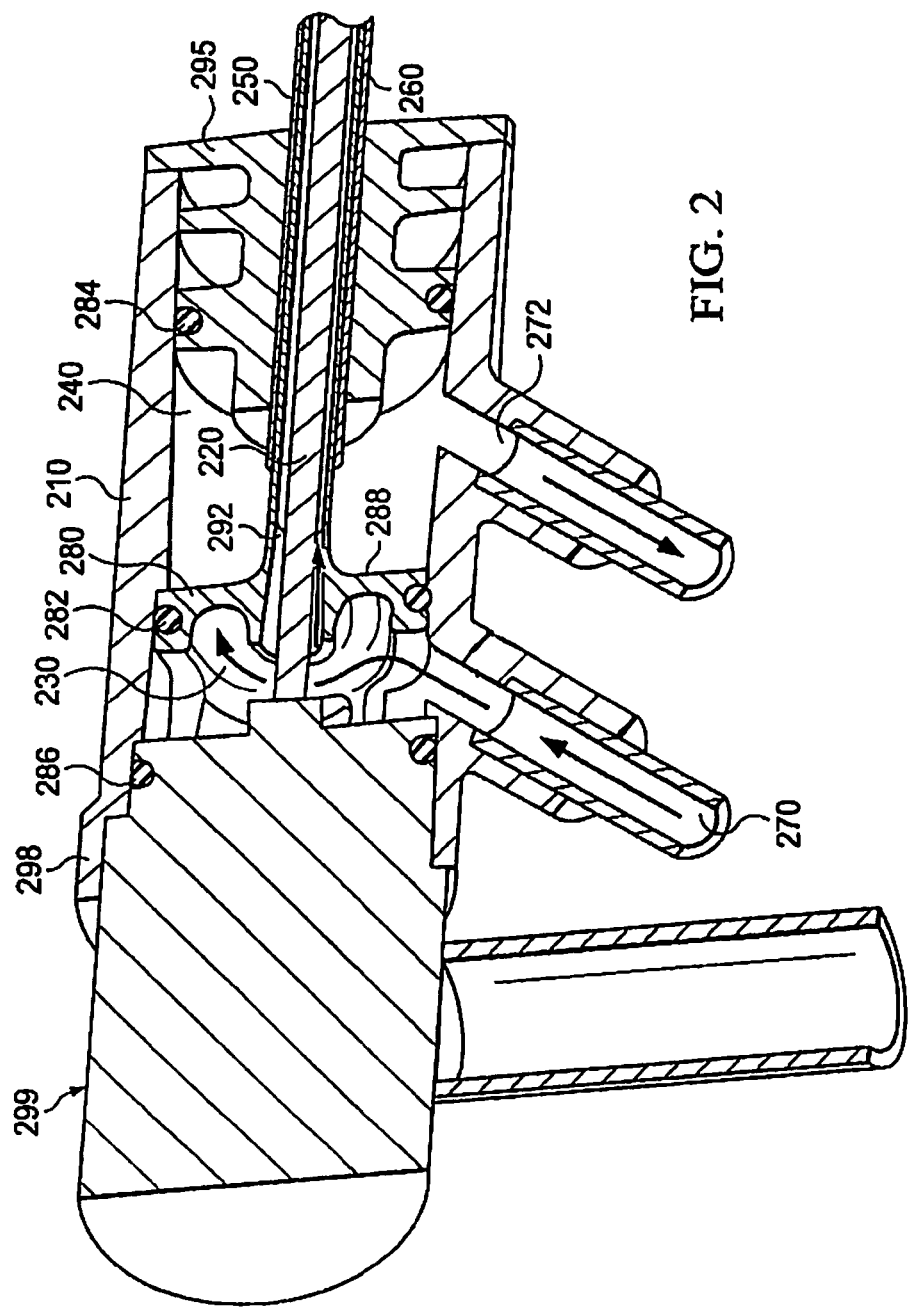
FIG. 2 is an alternate view of an embodiment of the invention showing twin chambers in a hub with inserts providing separation of the chambers.

FIG. 2 is a perspective view of an embodiment of the invention showing hub 210 and probe 220 extending from within the handle 299 out through the distal end of the hub 210. The probe 220 connects within the handle 299 to a power source (not shown). Hub 210 comprises a first chamber 230, a second chamber 240, a first lumen path 250, a second lumen path 260 and a first 270 and second 272 port. In an embodiment, the first 270 and second 272 ports are angled in relation to the axis of the hub 210 so that they are not perpendicular to the axis. The angle of the ports 270, 272 forms an acute angle toward the proximal end of the hub 210. The handle 299 forms a seal at the proximal end of the hub 210.

A first insert 280 forms the first chamber 230 between the handle 299 and the first insert 280. A second insert 295 forms the second chamber 240 between the first insert 280 and the second insert 295. The first chamber 230 is sealed by an o-ring 282 on the distal end of the chamber 230 and an o-ring 286 on the proximal end of the chamber 230. The second chamber 240 is sealed by o-ring 282 and an o-ring 284 on the distal end of the second chamber 240. Each O-ring 282, 284, 286 resides in a groove, or other formation, formed to receive the o-ring in the first insert 280, the second insert 295 and the handle 299, respectively.

The first lumen path 250 forms a fluid passage allowing a cooling fluid to travel from the first chamber 230 along the probe 220 to the distal end of the probe 220. The cooling fluid provides a cooling action along the length and tip (not shown) of the probe 220. The second lumen path 260 provides a return passage for the cooling liquid and is fluidicly coupled to the second chamber 240. The cooling liquid returns concentrically and outside the first lumen path 250 and empties into the second chamber 240.

Figure 3:
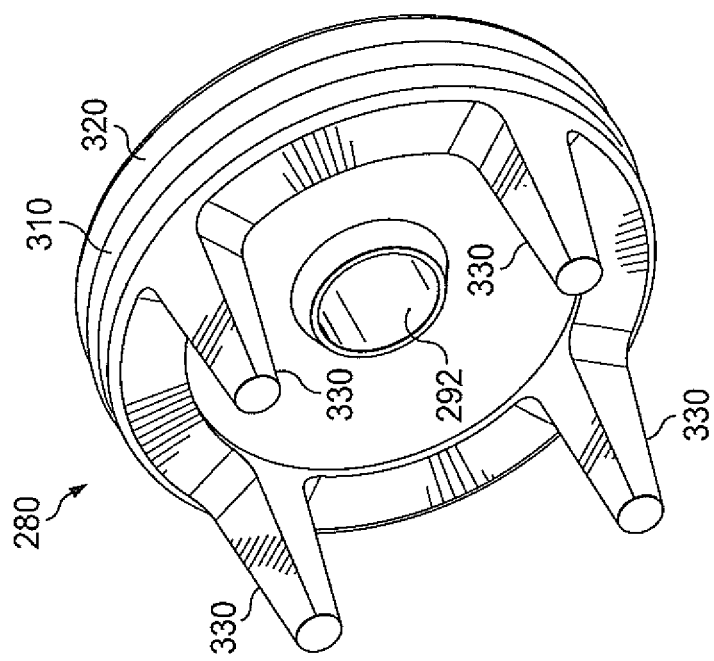
FIG. 3 is a view of an insert of an embodiment of the invention.

As noted above relating to FIGS. 1 and 2, the first insert (80 in FIG. 1 and 280 in FIG. 2) defines a boundary for the first chamber (30 in FIG. 1 and 230 in FIG. 2) and causes the cooling fluid to spin and thus reduce the presence of air bubbles. FIG. 3 provides a detailed view of the first insert 280. As noted above, the first insert 280 creates the first chamber (230 FIG. 2). The first insert 280 creates the chamber by using a seal 310 in the hub (210 FIG. 2). In an embodiment, the seal 310 is an o-ring which fits in a grooved portion 320, or other formed recess, of the insert. The grooved portion 320 is adapted to accommodate the o-ring 310.

Cooling fluid flows into the first chamber and fills the space within the first insert 280. The geometry 325 on the insert 280 is concave and induces spin in the cooling fluid as it enters the first chamber. The vortex type action induced on the cooling fluid allows it to move around the probe as it moves down the first lumen path. The vortex action aids in the elimination of air bubbles which may cause overheating of the probe.

The first insert 280 comprises a plurality of legs 330. In one embodiment, four legs 330 provide support for the first insert 280. The legs 330 provide a mechanism to abut the handle (not shown in FIG. 3) when the hub (not shown in FIG. 3) is assembled. The legs 330 will push against the handle to force the insert 280 against the stops on the interior of the hub.

Referring again to FIG. 1, regarding the operation of the invention. Cooling fluid flows into the first port 70 and fills the first chamber 30. In one embodiment, the first chamber 30 is sized so that it fills with fluid relatively rapidly. The first insert 80 is shaped so that the fluid entering the first chamber 30 spins in a circular manner. The spinning of the fluid causes any residual air bubbles to be removed from the probe 20 and the walls of the first chamber 30. Air bubbles are known in the art to cause over-heating of the probe 20 and lead to failure of the device. The o-ring 82 in the first insert 30 seals the chamber 30, thus not allowing fluid to enter the second chamber 40. It is understood by those skilled in the art that the first insert 30 provides sealing. The o-ring 82 provides an extra level of sealing to ensure integrity under pressure conditions.

The handle 100 has the O-ring 86 to create a seal on the back side of the first chamber 30. It is understood by those skilled in the art that the handle 100 provides a level of sealing. The o-ring 86 provides an extra level of sealing to ensure integrity under pressure conditions. The cooling fluid flows out of chamber 30 and through the first lumen path 50. The first lumen path 50 carries the cooling fluid to the proximal end of the probe 20 providing a cooling effect on the probe 20. The cooling fluid returns to the hub 10 via the second lumen path 60. The cooling fluid empties from the second lumen path 60 into the second chamber 40. The second chamber is sealed by the o-ring 82 on one end which is positioned in the first insert 80 and the o-ring 84 which is positioned in the second insert 95. It is understood by those skilled in the art that the second insert 95 provides a level of sealing. The o-ring 84 provides and extra level of sealing to ensure integrity under pressure conditions.

As the cooling fluid pressure increases in the hub 10, the pressure will cause a separating force on the components within the hub 10. This pressure will stress the position of the o-ring 82 in the first insert 80 and the o-ring 84 of the second insert 95. An external geometry (not shown) positioned on the outside of the handle 100 will hold the handle 100 in place and resist movement of the inserts 80, 95 and o-rings 82, 84.

Referring again to FIG. 2, the microwave assembly is easily manufactured with the hub 210, the first insert 280, the second insert 295 and the handle 299. The first insert 280 is inserted into the hub 210 until it abuts the stops 288 which are formed on the inside of the hub 210. The o-ring 282 in the first insert provides a seal against the interior wall of hub 210. In an embodiment, the wall of the hub 210 is graduated so that the circumference lessens toward the middle of the hub 210. The graduation levels off and ceases as the wall nears the stop 288 to allow a location for the o-ring 282 to seal.

The interior lumen path 260 connects to the central hole 292 in the first insert 280. The lumen paths 250, 260 protrude through the end of the hub 210. The second insert 295 is inserted over the lumen paths 250, 260 and into the distal end of the hub 210. O-ring 284 fits in a groove around the second insert 295 and forms a seal against the interior wall of the hub 210. In one embodiment, the wall at the distal end of the hub 210 is also graduated so that the circumference lessens toward the middle of the hub 210. The graduation levels off and ceases at a predetermined location which coincides with the position of the o-ring 284. The second insert 295 is molded to the distal end of the hub 210 to provide stability during high pressure situations.

The handle 299 and the probes are inserted into the proximal end of the hub 210. The probe 220 passes through the central holes in the inserts 280, 295 and helps create and enforce the lumen paths 250, 260. In an embodiment, the handle 299 and probe 220 are pre-assembled to maintain a sound electrical connection. A lip portion 298 extends from the portion of the hub 210 opposite the ports 270, 272. The lip portion 298 allows the insertion of the handle 299 in only one way to assure proper insertion of the handle 299. Insertion of the handle 299 provides sufficient pressure on the first insert 280 to maintain the insert 280 in the proper position. The stop 288 on the interior of the hub 210 wall prevents the first insert from being inserted too far inside the hub 210. The handle 299 is then molded to the hub 210.

It is understood that the above described embodiments are only illustrative of the application of the principles of the present disclosure. Numerous modifications and alternative arrangements may be devised by those skilled in the art without departing from the spirit and scope of the present disclosure. The appended claims are intended to cover such modifications and arrangements.

What is claimed is:

1. A microwave assembly, comprising:
a hub, the hub comprising a proximal end, a distal end, an input port and an output port;
a first insert, the first insert having a center hole;
a second insert; the second insert having a center hole, and an end portion;
a first lumen path and a second lumen path concentrically oriented respective to each other and wherein the first lumen path is connected to the center hole of the first insert and the second lumen path is connected to the center hole of the second insert;
a handle, the handle functionally connected to a probe;
a first chamber defined by the first insert; and
a second chamber defined by the first insert and the second insert,
wherein the first insert is inserted into the proximal end of the hub, the proximal end of the hub being adapted to receive the first insert, the second insert is inserted into the distal end of the hub, the hub adapted to receive the second insert, the first lumen path and the second lumen path extend through the center hole of the second insert and through the distal end of the hub, and the handle is inserted into the proximal end of the hub in abutting engagement with the first insert.

2. The microwave assembly of claim 1, wherein the hub further comprises an interior surface, and further comprising:
a first o-ring adapted to fit around the first insert creates a seal against the interior surface;
a second o-ring adapted to fit around the handle creates a seal against the interior surface; and
a third o-ring adapted to fit around the second insert creates a seal against the interior surface.

3. The microwave assembly of claim 2, wherein the first chamber is between the first and second o-rings and the second chamber is between the first and third o-rings, wherein the first chamber is in fluid communication with the input port and the second chamber is in fluid communication with the output port.

4. The microwave assembly of claim 1, wherein the second insert is attached to the distal end of the hub.

5. The microwave assembly of claim 1, wherein the hub comprises a stop in the interior surface and the first insert abuts the stop.

6. The microwave assembly of claim 1, wherein the hub comprises a stop in the interior surface and the first insert abuts the stop, and the interior surface circumferentially decreases from the proximal end to a predetermined location toward a center point of the hub and ceases to decrease circumferentially before the stop; and wherein the interior surface circumferentially decreases from the distal end to a predetermined location toward the center point of the hub and ceases to decrease circumferentially.

7. The microwave assembly of claim 1, wherein the hub comprises a stop in the interior surface and the first insert abuts the stop, the interior surface circumferentially decreases from the proximal end to a predetermined location toward a center point of the hub and ceases to decrease circumferentially before the stop; and wherein the interior surface circumferentially decreases from the distal end to a predetermined location toward the center point of the hub and ceases to decrease circumferentially, and the hub further comprises an extension adapted to extend laterally away from the center of the hub and to engage the handle to disallow incorrect insertion of the handle into the proximal end of the hub.

\* \* \* \* \*